Oct. 19, 1971 R. KORDES Plant Pat. 3,078
ROSE PLANT
Filed Aug. 22, 1969
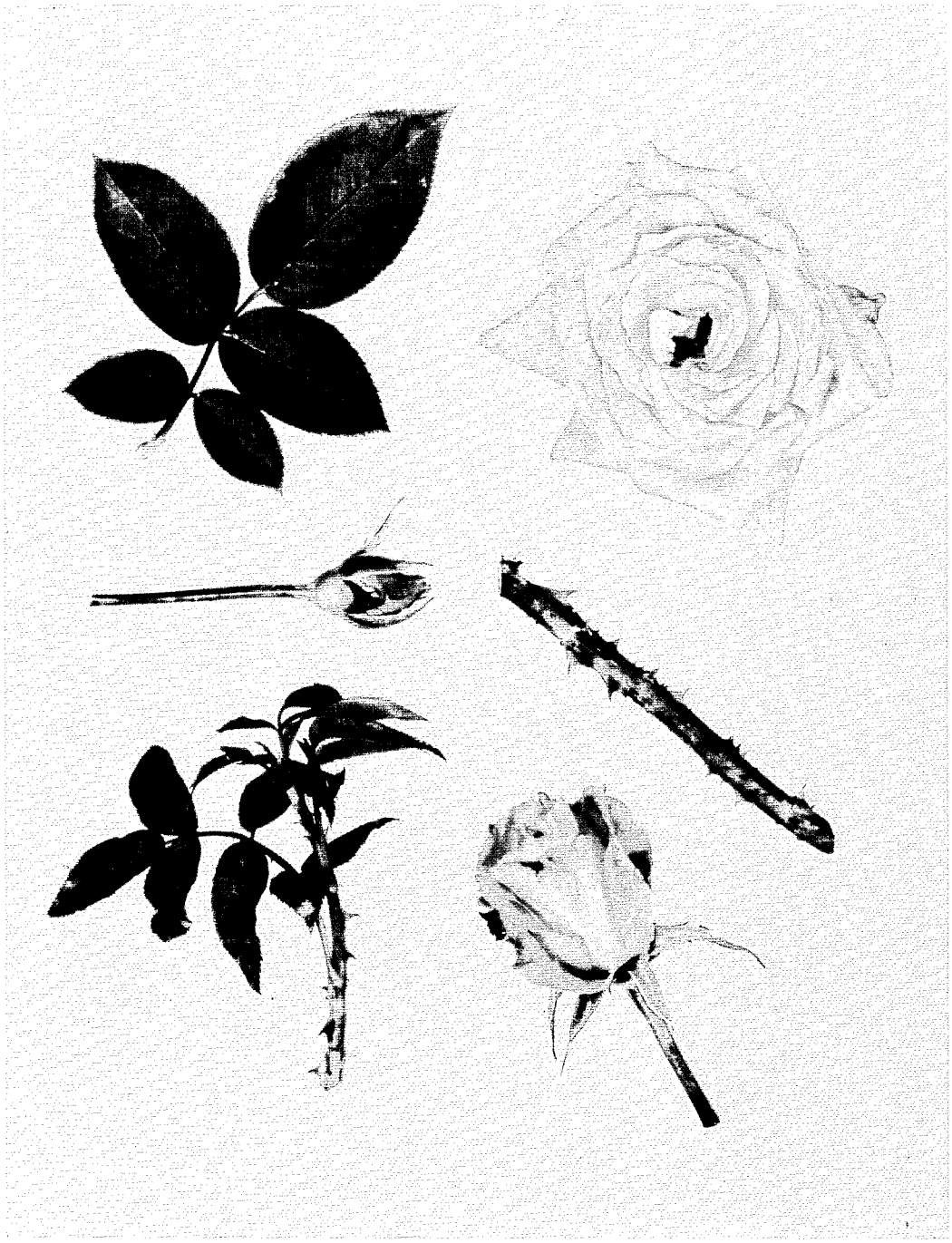
Inventor.
Reimer Kordes
By: Robb & Robb
attorneys.

United States Patent Office

Plant Pat. 3,078
Patented Oct. 19, 1971

3,078
ROSE PLANT

Reimer Kordes, Holstein, Germany, assignor to Jackson & Perkins Company, Newark, N.Y.

Filed Aug. 22, 1969, Ser. No. 852,517
Int. Cl. A01h 5/00
U.S. Cl. Plt.—19 1 Claim The present invention relates to a new and distinct variety of rose plant of the hybrid tea class, which was originated by me by crossing the rose variety known as "Detroiter" (U.S. Plant Patent No. 1,219) with the rose variety known as "Orange Delbard" (unpatented), the former being the seed parent and the latter being the pollen parent.

The primary objective of this breeding was to produce a new and improved rose variety of the hybrid tea class, which bears large flowers of scarlet color on a well-branched and vigorous plant. This objective was fully achieved, along with other desirable improvements, as evidenced by the following unique combination of characteristics which are outstanding in the new variety and which distinguish it from its parents, as well as from all other rose varieties of which I am aware:

(1) A vigorous and heavily branched plant habit, with the branches originating mostly near the base of the plant;
(2) Unusually large flowers;
(3) A distinctive and attractive flower color ranging between Rose Doree and Scarlet, said color being uniform in the half-open blooms but lightening to Geranium Pink after several days; and
(4) A moderately strong and fruity flower fragrance.

Asexual reproduction of my variety by budding, as performed by me in Germany and on my behalf at Wasco, Calif., U.S.A., shows that the foregoing charteristics and distinctions come true to form and are estabiished and transmitted through succeeding propagations.

The accompanying drawing shows typical specimens of the vegetative growth and flowers of my new variety in different stages of development and as depicted in color as nearly true as it is reasonably possible to make the same in a color illustration of this character.

The following is a detailed description of the new rose variety, with color terminology in accordance with Ridgway's Color Standards and Nomenclature, except where general color terms of ordinary dictionary significance are obvious:

Parentage: Seedling.
*Seed parent.*—"Detroiter."
*Pollen parent.*—"Orange Delbard."
Classification:
*Botanic.*—Rosa hybrid.
*Commercial.*—Hybrid tea.
Propagation: Holds its distinguishing characteristics through succeeding propagations by budding.

*Flower*

(Observations made from specimens grown at Newark, N.Y., U.S.A., in the afternoon during early July.)

Blooming habit:
*Recurrent.*—Continuous.
Bud:
*Size.*—Very large; pointed; ovoid.
*Color.*—When sepals first divide—Nopal Red, Plate 1,3 i. When half-blown—Inside of petals—Rose Doree, Plate 1,3b. Reverse of petals—Eosine Pink, Plate 1,1 d.

*Sepals.*—Lightly appendaged; hairy edge. Color—Inside—Lumiere Green, Plate 17,29′ b. Outside—Apple Green, Plate 17,29′, heavily overlaid with Morocco Red, Plate 1,5 k.
*Receptacle.*—Color—Apple Green, Plate 17,29′, Shape—Funnel. Size—Broad. Surface—Smooth.
*Peduncle.*—Length—Short. Surface—Prickly. Color—Apple Green, Plate 17,29′. Strength—Stiff; erect.
*Opening.*—Outer petals lightly recurve; no quilling; center usually covered.
Bloom:
*Size.*—Very large; from 5 inches to 6 inches.
*Borne.*—Singly.
*Stem.*—Medium length.
*Form.*—High-centered. Permanence—Retains its form to the end.
*Petalage.*—Number of petals under normal conditions—From 35 to 40.
*Color.*—Center of flower—Upper side of petals—Between Rose Doree, Plate 1,3 b and Scarlet, Plate 1,5. Reverse of petals—Eosine Pink, Plate 1,1 d. Outer petals—Upper side—Rose Doree, Plate 1,3 b, overlaid on outer edges with Scarlet Red, Plate 1,3. Reverse side—Eosine Pink, Plate 1,1 d, overlaid on outer edges with Scarlet Red, Plate 1,3. Base of petals—Very small area of white color. General tonality from a distance—Between Rose Doree and Scarlet.
*Discoloration.*—Slightly lighter than Rose Doree, shading to Geranium Pink, Plate 1,3 d about third day.
*Fragrance.*—Moderate. Nature—Fruity.
Petals:
*Texture.*Thin.
*Surface.*—Inside—Satiny. Reverse—Satiny.
*Shape.*—Round.
*Form.*—Tips slightly recurved.
*Arrangement.*—Imbricated.
*Resistance.*—Drop off cleanly.
*Lasting quality.*—On the plant—Fair. As cut flower—Fair.

*Reproductive organs*

Anthers: Medium size; arranged regularly around styles. Color—Yellow.
Filaments (threads): Medium length. Color—Eosine Pink, Plate 1,1 d.
Pollen: Color—Lemon yellow.
Styles: Loosely separated.
Stigmas: Color—Yellow.
Ovaries: All enclosed in calyx.
Fruit: None observed.

*Plant*

Form: Bush.
Growth: Very vigorous.
Foliage: Compound of 5 leaflets on normal mid-stem leaves.
*Size.*—Large.
*Quantity.*—Abundant.
*Color.*—New foliage—Upper side—Garnet Brown, Plate 1,3 k. Reverse side—Burnt Lake, Plate 12,71 m. Old foliage—Upperside—Varley's Green, Plate 18,31′ m. Reverse side—Slightly lighter than Chromium Green, Plate 32,31″ i.
*Leaflets.*—Shape—Oval pointed. Texture—Upper side—Leathery. Under side—Smooth. Ribs and veins—Prominent. Edge—Serrated. Serration—Single; small. Petiole (rachis)—Color—Green. Under side—Prickly. Stipules—Short; smooth.

Disease resistance—Normal resistance to mildew and blackspot, as determined by comparison with other rose variety grown under the same conditions at Newark, N.Y., U.S.A.

Wood:

*New wood.*—Color—Light green. Bark—Smooth.

*Old wood.*—Color—Green. Bark—Smooth.

Thorns:

*Thorns.*—Quantity—On main stalks from base—Many. On laterals from stalk—Many. Form—Broad base; slightly hooked downward. Color (when young)—Morocco Red, Plate 1,5 k. Position—Irregular.

*Prickles.*—*Quantity*—On main stalks—Few. On laterals—Few.

*Short needles.*—Quantity—On main stalks—Many. On laterals—Many.

I claim:

1. A new and distinct variety of rose plant of the hybrid tea class, substantially as herein shown and described, characterized particularly as to novelty by the unique combination of a vigorous and heavily branched plant habit, with the branches originating mostly near the base of the plant, unusually large flowers, a distinctive and attractive flower color ranging between Rose Doree and Scarlet, said color being uniform in the half-open blooms but lightening to Geranium Pink after several days, and a moderately strong and fruity flower fragrance.

No references cited.

ROBERT E. BAGWILL, Primary Examiner